(12) United States Patent
Baynham et al.

(10) Patent No.: US 8,172,905 B2
(45) Date of Patent: May 8, 2012

(54) SPINAL IMPLANT

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 1126 days.

(21) Appl. No.: 11/741,249

(22) Filed: Apr. 27, 2007

(65) Prior Publication Data
US 2008/0269901 A1 Oct. 30, 2008

(51) Int. Cl.
*A61F 2/44* (2006.01)
(52) U.S. Cl. ..................................... 623/17.16
(58) Field of Classification Search ..... 623/17.11–17.16
See application file for complete search history.

(56) References Cited

U.S. PATENT DOCUMENTS

| | | | |
|---|---|---|---|
| 4,016,863 A | 4/1977 | Brantigan | |
| 4,349,921 A | 9/1982 | Kuntz | |
| 4,743,256 A | 5/1988 | Brantigan | |
| 4,834,757 A | 5/1989 | Brantigan | |
| 4,878,915 A | 11/1989 | Brantigan | |
| 5,015,247 A | 5/1991 | Michelson | |
| 5,192,327 A | 3/1993 | Brantigan | |
| 5,425,772 A | 6/1995 | Brantigan | |
| 5,645,598 A | 7/1997 | Brosnahan, III | |
| 5,658,336 A * | 8/1997 | Pisharodi | 623/17.16 |
| 5,665,122 A | 9/1997 | Kambin | |
| 5,766,253 A | 6/1998 | Brosnahan, III | |
| 5,865,847 A | 2/1999 | Kohrs et al. | |
| 5,888,222 A * | 3/1999 | Coates et al. | 623/17.16 |
| 6,080,158 A * | 6/2000 | Lin | 606/247 |
| 6,090,143 A | 7/2000 | Meriwether et al. | |
| 6,096,080 A | 8/2000 | Nicholson et al. | |
| 6,102,948 A | 8/2000 | Brosnahan, III | |
| 6,123,705 A | 9/2000 | Michelson | |
| 6,149,686 A | 11/2000 | Kuslich et al. | |
| 6,159,245 A | 12/2000 | Meriwether et al. | |
| 6,224,595 B1 | 5/2001 | Michelson | |
| 6,241,733 B1 | 6/2001 | Nicholson et al. | |
| 6,241,769 B1 | 6/2001 | Nicholson et al. | |
| 6,258,094 B1 | 7/2001 | Nicholson et al. | |
| 6,261,293 B1 | 7/2001 | Nicholson et al. | |
| 6,261,295 B1 | 7/2001 | Nicholson et al. | |
| 6,267,763 B1 | 7/2001 | Castro | |
| 6,290,724 B1 * | 9/2001 | Marino | 623/17.11 |
| 6,312,431 B1 | 11/2001 | Asfora | |
| 6,488,710 B2 | 12/2002 | Besselink | |
| 6,530,955 B2 | 3/2003 | Boyle et al. | |
| 6,576,016 B1 | 6/2003 | Hochshuler et al. | |
| 6,582,431 B1 | 6/2003 | Ray | |
| 6,666,889 B1 | 12/2003 | Commarmond | |
| 6,679,887 B2 | 1/2004 | Nicholson et al. | |

(Continued)

*Primary Examiner* — Eduardo C Robert
*Assistant Examiner* — Jerry Cumberledge
(74) *Attorney, Agent, or Firm* — McHale & Slavin, P.A.

(57) ABSTRACT

A spinal implant for insertion in the intervertebral space is formed as a hollow cage, wedge shaped in profile, with a lesser height leading end for a low profile entry. The cage has two open sides with a plurality of angled teeth along opposite longitudinal edges for engaging the end plates of adjacent vertebrae when the cage is rotated into position. One portion of the angled teeth are angled toward an end of the cage and another portion of the angled teeth are angled away from that end to provide a lock preventing the cage from migrating ventrally or dorsally from the spine. Upon rotation, the leading end has a greater height than the trailing end.

9 Claims, 4 Drawing Sheets

U.S. PATENT DOCUMENTS

Figure 1:
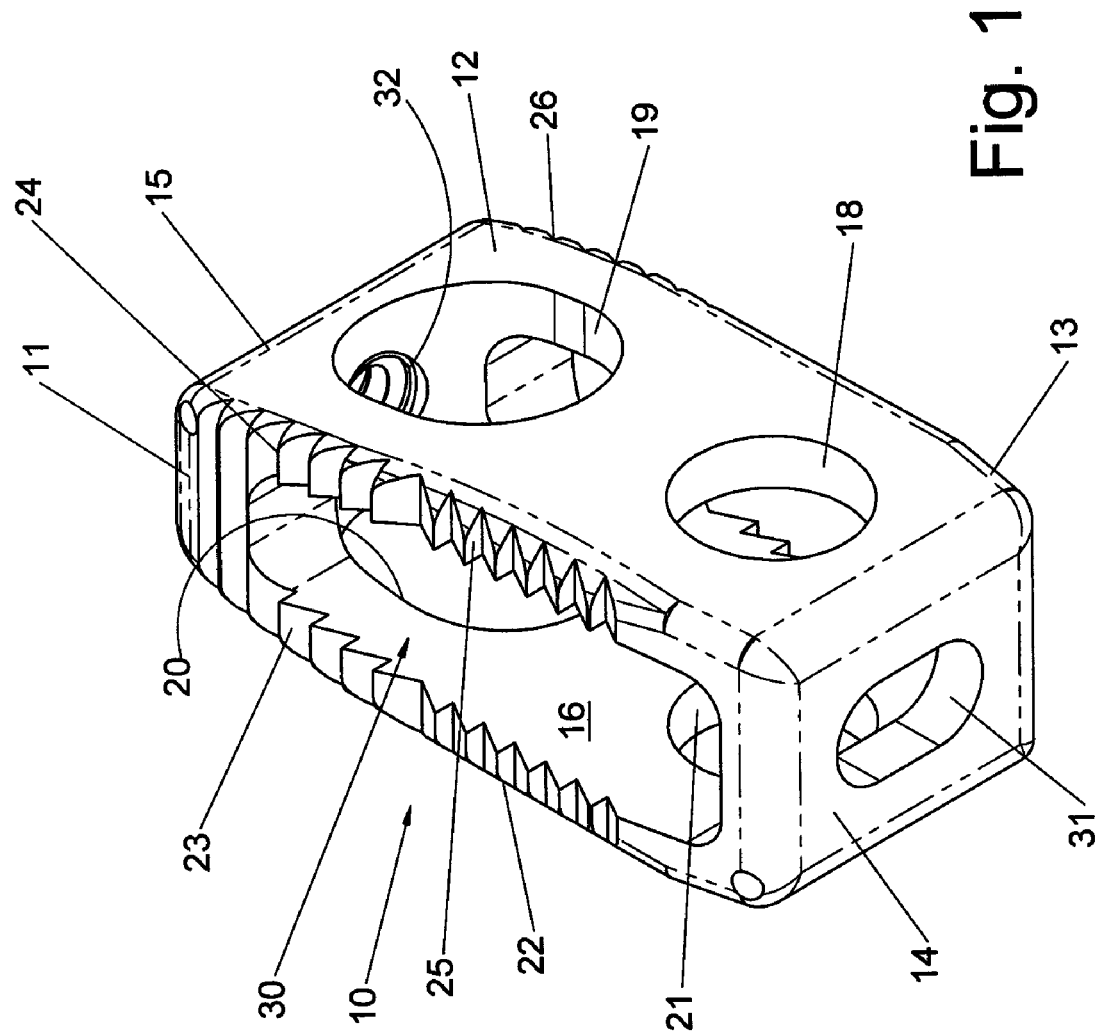

| | | |
|---|---|---|
| 6,743,255 B2 | 6/2004 | Ferree |
| 6,746,484 B1 | 6/2004 | Liu et al. |
| 6,767,366 B2 * | 7/2004 | Lee et al. .................... 623/17.16 |
| 6,800,093 B2 | 10/2004 | Nicholson et al. |
| 6,805,697 B1 | 10/2004 | Helm et al. |
| 6,827,743 B2 | 12/2004 | Eisermann et al. |
| 6,942,697 B2 | 9/2005 | Lange et al. |
| 7,018,412 B2 | 3/2006 | Ferreira et al. |
| D524,443 S * | 7/2006 | Blain .......................... D24/155 |
| 7,135,043 B2 | 11/2006 | Nakahara et al. |
| 7,169,183 B2 * | 1/2007 | Liu et al. ................... 623/17.16 |
| 7,320,686 B2 | 1/2008 | Serhan et al. |
| 7,588,599 B2 | 9/2009 | Sweeney |
| 2002/0032483 A1 | 3/2002 | Nicholson et al. |
| 2002/0123750 A1 | 9/2002 | Eisermann et al. |
| 2003/0023306 A1 * | 1/2003 | Liu et al. ................... 623/17.11 |
| 2003/0097136 A1 | 5/2003 | Hajianpour |
| 2003/0153975 A1 | 8/2003 | Byrd, III et al. |
| 2003/0232065 A1 | 12/2003 | Remington et al. |
| 2003/0233147 A1 | 12/2003 | Nicholson et al. |
| 2004/0006125 A1 | 1/2004 | Remington et al. |
| 2004/0186572 A1 | 9/2004 | Lange et al. |
| 2004/0215202 A1 | 10/2004 | Preissman |
| 2005/0038514 A1 | 2/2005 | Helm et al. |
| 2005/0043733 A1 | 2/2005 | Eisermann et al. |
| 2005/0070900 A1 | 3/2005 | Serhan et al. |
| 2005/0119747 A1 | 6/2005 | Monterumici et al. |
| 2005/0246021 A1 | 11/2005 | Ringeisen et al. |
| 2005/0273166 A1 | 12/2005 | Sweeney |
| 2006/0167548 A1 | 7/2006 | Jackson |
| 2006/0217806 A1 | 9/2006 | Peterman |
| 2006/0247771 A1 | 11/2006 | Peterman |
| 2007/0050031 A1 | 3/2007 | Khosrowshahi |
| 2007/0093898 A1 | 4/2007 | Schwab |
| 2007/0270956 A1 | 11/2007 | Heinz |
| 2008/0288076 A1 * | 11/2008 | Soo et al. ................... 623/17.16 |
| 2009/0312837 A1 | 12/2009 | Eisermann et al. |

* cited by examiner

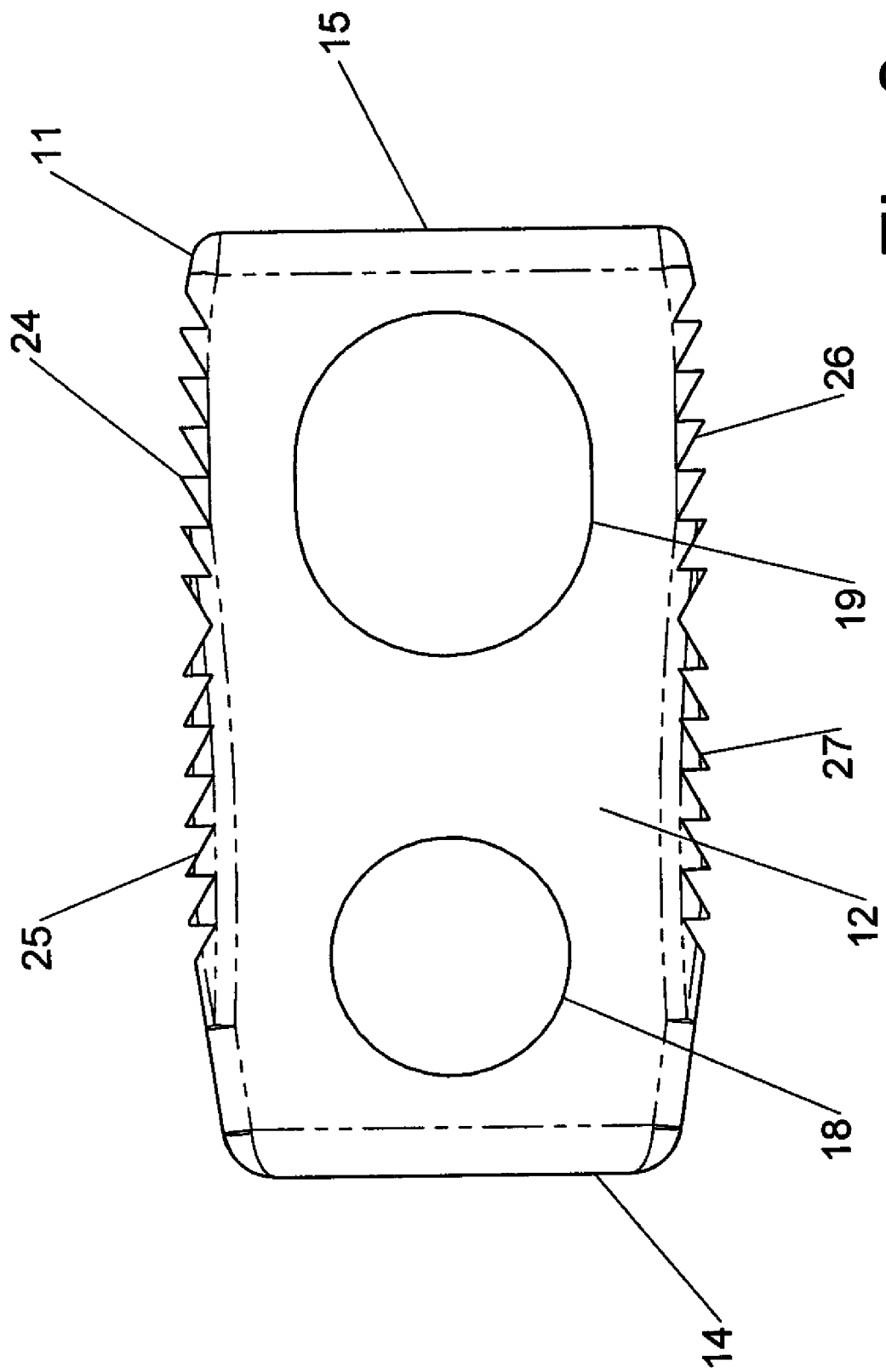

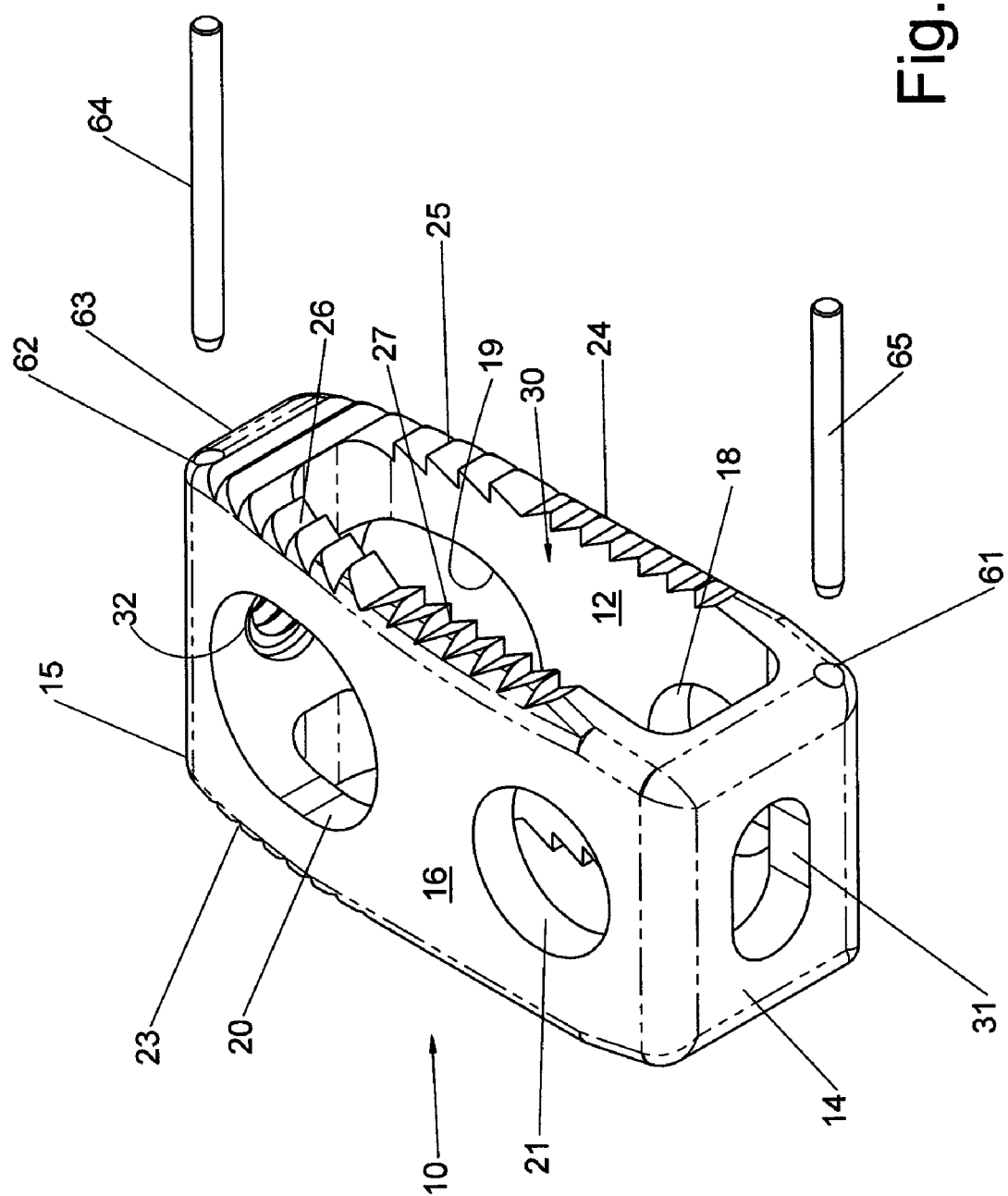

SPINAL IMPLANT

BACKGROUND OF THE INVENTION

1. Field of the Invention

This invention relates to spinal implants inserted between adjacent vertebrae to stabilize the intervertebral space and correct the angle of the spine. The implant also facilitates fusion of the affected vertebrae.

2. Description of the Prior Art

The spinal cage is a well known device for insertion between vertebrae to provide support in lieu of the natural spinal disc. The cages may be of different shapes, including rectangle, cylinder and wedge, enclosing an interior filled with bone growth material, among other compositions, which promote the fusion of the vertebrae on each side of the cage. The cages are open structures which allow vascularization and bone in-growth.

It is very important that these cages be prevented from migrating out of the prepared surgical site because any movement will prolong the fusion process and traumatize healthy tissue.

U.S. Pat. No. 6,746,484 B1 to Liu et al illustrates such a wedge shaped cage with rectilinear ends. Liu et al is directed to proper placement of the cage so that the large and small ends of the wedge are support members and the interconnected sides facilitate fusion or bone growth. Distractors with screw-like threads are used to form a shaped bed in the end plates of the adjacent vertebrae to accept the cage. The cage has two open opposite long sides and two closed long sides. The filled cage is inserted into the prepared site and rotated 90 degrees so that the open sides will be in contact with the end plates of the adjacent vertebrae. The cage is held in place by compression between the vertebrae.

U.S. Pat. No. 5,425,772 to Brantigan is directed to another wedge shaped implant similar to the cage described above. The surgical site is prepared by cutting slots in the adjacent vertebrae end plates and separating the end plates by distraction. The closed long sides have a series of sharpened ridges or teeth extending across the closed sides parallel to the ends. The teeth are shaped as elongated isosceles triangles for biting into the adjacent vertebrae surfaces when implanted. The valleys between the teeth are filled with bone growth material to promote fusion. After implantation, the distraction is released to reduce the space between the vertebrae and to seat the implant by compression.

What is lacking in the prior art is a spinal cage which has a large open vertebral contact area for boney in-growth and a locking structure to prevent ventral and dorsal movement after implantation and a cage that can provide lordosis, mimicing the natural curvature of the spine.

SUMMARY OF THE PRESENT INVENTION

Therefore, an object of this invention is to provide a spinal implant sized and shaped to support adjacent vertebrae in the proper angular and spatial relationship.

It is another object of this invention to provide a spinal implant cage with a hollow interior to serve as a reservoir of bone growth material and to provide a large contact area between the material and the vertebrae.

It is a further object of this invention to provide a plurality of angled teeth securing the cage to the end plates of the vertebrae and preventing migration of the implant from the implant site.

It is yet another object of this invention to provide a method of implanting the cage by rotation of the cage to engage the angled teeth in the end plates of the vertebrae.

It is a still further object of this invention to provide a wedge shape in which the major distraction distance shifts from the trailing end to the leading end as the cage is rotated.

SHORT DESCRIPTION OF THE DRAWINGS

Figure 2:
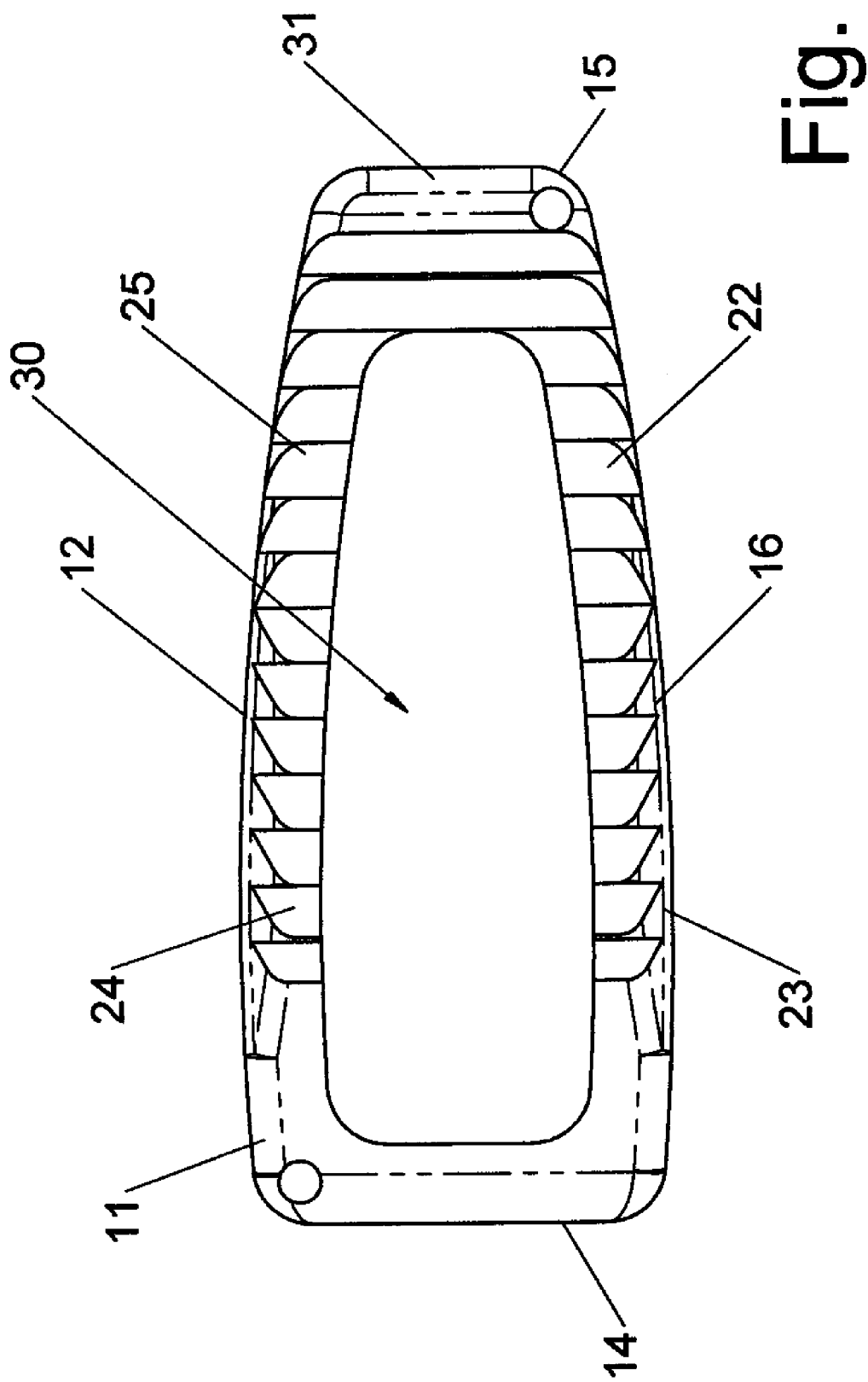

FIG. 1 is a perspective of the spinal cage of this invention;
FIG. 2 is a top plan view of the cage of FIG. 1;
FIG. 3 is a side plan view of the cage of FIG. 1; and
FIG. 4 is an exploded perspective of another embodiment of the cage of this invention.

DETAILED DESCRIPTION OF THE INVENTION

The spinal implant is formed as a cage 10 with a hollow interior 30, as shown in FIG. 1, surrounded by an open framework. The cage shown in FIGS. 1, 2, and 3 has an overall shape of a wedge with a smaller end wall 14 and a larger end wall 15. As shown in FIGS. 1 and 4, the leading end 15 is longer than trailing end 14. Elongated sidewalls 12 and 16 connect the ends and are disposed diametrically opposite to each other. Sidewall 12 has apertures 18 and 19 which communicate with the interior 30. Sidewall 16 is a mirror image of sidewall 12 and includes apertures 20 and 21. The apertures in the sidewalls may be the same size or different sizes, as shown. The apertures contribute to the integration of the implant into spine. The cage may be made of surgical stainless steel, titanium, other metallic alloys, ceramics, polymeric material or combinations thereof that are bio-compatible and have sufficient strength to support adjacent vertebrae in desired spatial relationship with proper curvature of the spine.

Along the longitudinal periphery of the sidewall 12 is a series of teeth terminating in a sharpened apex. On one portion of the periphery the teeth 24 and 26 are angled away from the small end 14. In the other portion of the periphery of sidewall 12, the teeth 25 and 27 are angled toward the small end wall 14, as shown in FIG. 3. The periphery of sidewall 16 is similarly shaped with the teeth 22 angled away from the small end wall 14 and the teeth 23 angled toward the small end wall 14. The angled teeth gain purchase in the bone and act as a ratchet to prevent relative movement between the implant and the end plates of the adjacent vertebrae. The opening 30 between the periphery of side walls 12 and 16 communicates with the hollow interior of the cage. When the cage is filled with bone growth and/or other material, this large opening on either side of the cage provides a large contact area to promote boney ingrowth, vascularization and fusion of the adjacent vertebrae.

The end smaller wall 14, shown in FIG. 1, has an oblong opening 31 which mates with an implant tool (not shown) used to manipulate the implant for permanent positioning in the spine. The longer end wall 15 has a threaded opening 32 opposite the opening 31 to which the implant tool may be removably connected. These openings, 31 and 32, may be reversed.

The manipulation would normally include insertion through a percutaneous opening in the patient's back and sliding the implant into a prepared site between lumbar vertebrae. The longer end wall 15 is the leading end with the smooth width of one of the sidewalls contacting the upper vertebrae and the other sidewall contacting the lower vertebrae. To this end, the sidewalls 12 and 16 are bowed outwardly in an arc increasing the volume of the hollow interior and reducing the area of sliding contact with the vertebral end plates. Also, the end walls 14 and 15 may be rectilinear with the sidewalls connecting the opposite sides of the rectangles so that the implant has a low profile during insertion within the prepared spinal site. The low profile leading end is shown in the insertion phase in FIG. 2.

Once within the spinal site, the implant is rotated approximately 90 degrees to orient the width of the sidewalls of the implant more or less parallel with the longitudinal axis of the spine and engage the teeth with the end plates of the adjacent vertebrae. The rotation results in increasing the profile of the cage at the leading end and reducing the profile at the trailing end, as shown by a comparison of FIG. 2 and FIG. 3.

The implant tool is then removed. The hollow interior 30 of the cage may then be filled with a composition including bone growth material, bone cement, bone particles, and other structural or pharmaceutical components, alone or in combination. In the alternative, the interior of the cage may be filled with the desired material before insertion into the patient. In the final position, the bone growth material is in contact with the end plates of the vertebrae through the large openings on both sides of the implant.

FIG. 4 illustrates another embodiment of the cage which may have a rectilinear shape and radiopaque markers useful during the surgical implantation to locate the forward and rear ends of the cage in relation to the spine for proper placement of the cage. The end walls 14 and 15 each have an opening 61 connecting to a bore 63 along one edge, respectively. Radiopaque rods 64 and 65 are secured in the bores. During the surgical procedure of implantation, the proper positioning of the implant may be monitored by fluoroscope.

The cage 10 may be constructed as a molded, cast or machined unitary structure or as a construct of components. The end walls and the sidewalls may be separate elements connected together by welding, adhesives, heat and pressure, or other fastening. The teeth may be integral with the sidewalls or separate pieces attached to the periphery of the sidewalls.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A spinal implant for stabilizing intervertebral space between adjacent vertebrae and maintaining curvature of the spine comprising a cage with a hollow interior and having a first end and a second end, a first elongated side connecting said first end and said second end, a second elongated side connecting said first end and said second end, said second elongated side diametrically opposed to said first elongated side about said hollow interior, said first elongated side and said second elongated side spaced apart forming an opening communicating with said hollow interior, said opening having a periphery defined by the edges of said first elongated side and said second elongated side, said periphery including a plurality of angled teeth, a first portion of said plurality of teeth angled toward said first end and a second portion of said plurality of teeth angled away from said first end, said first end being longer than said second end, said first elongated side and said second elongated side extending toward each other to form a wedge, said wedge adapted to contact adjacent vertebrae to maintain curvature of the spine, said first end having a rectilinear shape with two opposite long sides connected to two opposite short sides, said second end having a rectilinear shape with two opposite long sides connected to two opposite short sides, said first elongated sidewall attached to one long side of said first end and said second elongated sidewall attached to a second long side of said first end, said second end having a rectilinear shape with two opposite sides shorter than said opposite long sides of said first end, said first elongated sidewall attached to one shorter side of said second end and said second elongated sidewall attached to the opposite shorter side of said second end.

2. A spinal implant for stabilizing adjacent vertebrae and maintaining curvature of the spine of claim 1 comprising said first elongated side and said second elongated side formed in an arc between said first end and said second end, said arc increasing said hollow interior of said cage.

3. A spinal implant for stabilizing adjacent vertebrae and maintaining curvature of the spine of claim 1 comprising a bone growth material disposed in said hollow interior, said bone growth material adapted to contact adjacent vertebrae through said opening.

4. A spinal implant for low profile insertion in the intervertebral space between adjacent vertebrae and maintaining curvature of the spine comprising a cage with a hollow interior and having a leading end and a trailing end, said leading end being rectilinear with two opposite short sides connected to two opposite long sides, said trailing end being rectilinear with two opposite short side connected to two opposite long sides, a first cage wall connected to one of said opposite long sides, a second cage wall connected to the other of said opposite long sides, said cage adapted to be inserted between adjacent vertebrae with said first cage wall and said second cage wall contacting the end plates of the vertebrae, said trailing end having a rectilinear shape with opposed sides, said first cage wall connected to a side of said trailing end shorter than one of said long sides of said leading end, said second cage wall connected to the opposed side of said trailing end shorter than the other of said opposite long sides of said leading end, said first cage wall and said second cage wall forming said hollow interior whereby upon insertion and rotation, said cage is adapted to increase the intervertebral space at said leading end, said first cage wall and said second cage wall having a first width at said leading end and a second smaller width at said trailing end whereby upon rotation said intervertebral space at said leading end increases and said vertebral space at said trailing end decreases.

5. A spinal implant for low profile insertion in the intervertebral space between adjacent vertebrae and maintaining curvature of the spine of claim 4 comprising said cage having a wedge shape with said first cage wall and said second cage wall sloping outwardly from said leading end toward said trailing end.

6. A spinal implant for low profile insertion in the intervertebral space between adjacent vertebrae and maintaining curvature of the spine of claim 5 comprising first cage wall and said second cage wall having a first width at said leading end and a second smaller width at said trailing end whereby upon rotation said intervertebral space at said leading end increases and said vertebral space at said trailing end decreases.

7. A spinal implant for low profile insertion in the intervertebral space between adjacent vertebrae and maintaining curvature of the spine of claim 4 comprising said first cage wall and said second cage wall each having an arcuate shape between said leading end and said trailing end increasing said hollow interior, said arcuate shape adapted to aid in placement of said implant.

8. A spinal implant for low profile insertion in the intervertebral space between adjacent vertebrae and maintaining curvature of the spine of claim 4 comprising said first cage wall and said second cage wall each having opposite edges, said edges formed with angled teeth and means for rotating said cage to engage said angled teeth with adjacent vertebrae.

9. A spinal implant for low profile insertion in the intervertebral space between adjacent vertebrae and maintaining curvature of the spine of claim 4 comprising at least one radiopaque marker in said cage.

\* \* \* \* \*